(12) United States Patent
Zigmantas et al.

(10) Patent No.: US 11,286,345 B2
(45) Date of Patent: Mar. 29, 2022

(54) BIODEGRADABLE CATIONIC POLYMERS AND USES THEREOF

(71) Applicant: THERMO FISHER SCIENTIFIC BALTICS UAB, Vilnius (LT)

(72) Inventors: Sarunas Zigmantas, Vilnius (LT); Lolita Zaliauskiene, Vilnius (LT); Ricardas Makuska, Vilnius (LT); Alma Bockuviene, Vilnius (LT); Ausvydas Vareikis, Vilnius (LT)

(73) Assignee: Thermo Fisher Scientific Baltics UAB, Vilnius (LT)

( * ) Notice: Subject to any disclaimer, the term of this patent is extended or adjusted under 35 U.S.C. 154(b) by 609 days.

(21) Appl. No.: 16/078,593

(22) PCT Filed: Mar. 10, 2017

(86) PCT No.: PCT/US2017/021888
§ 371 (c)(1),
(2) Date: Aug. 21, 2018

(87) PCT Pub. No.: WO2017/156447
PCT Pub. Date: Sep. 14, 2017

(65) Prior Publication Data
US 2019/0048139 A1    Feb. 14, 2019

Related U.S. Application Data

(60) Provisional application No. 62/310,320, filed on Mar. 18, 2016, provisional application No. 62/307,322, filed on Mar. 11, 2016.

(51) Int. Cl.
*C08G 73/02*    (2006.01)
*C08G 75/00*    (2006.01)
*A61K 47/59*    (2017.01)
*A61K 31/713*   (2006.01)
*A61K 47/34*    (2017.01)
*C12N 15/113*   (2010.01)

(52) U.S. Cl.
CPC ........ *C08G 73/0253* (2013.01); *A61K 31/713* (2013.01); *A61K 47/34* (2013.01); *A61K 47/59* (2017.08); *C08G 73/0206* (2013.01); *C08G 75/00* (2013.01); *C12N 15/113* (2013.01); *C12N 2310/14* (2013.01); *C12N 2320/32* (2013.01)

(58) Field of Classification Search
CPC ...... A61K 31/713; A61K 47/34; A61K 47/59; C08G 73/0206; C08G 73/0253; C08G 75/00; C12N 15/113; C12N 2310/14; C12N 2320/32
USPC .................................................. 424/450, 486
See application file for complete search history.

(56) References Cited

U.S. PATENT DOCUMENTS 9,102,796 B2 * 8/2015 Lagunavicius ........ A61K 47/59
2007/0182791 A1    8/2007 Chung et al.

FOREIGN PATENT DOCUMENTS

EP          2070970          6/2009
WO    WO-2012101455 A1 *  8/2012   ........... A61K 31/197

OTHER PUBLICATIONS

Lin et al. Bioconjugate Chem. 2007, 18, 138-145 (Year: 2007).*
PCT/US2017/021888, "International Search Report", dated Jun. 28, 2017, 5 Pages.

* cited by examiner

*Primary Examiner* — Janet L Epps-Smith

(57) ABSTRACT

Disclosed herein are poly(hydroxylalkyleneimine disulfide) polymers, which have both desirable transfection properties and reduced toxicity.

16 Claims, 8 Drawing Sheets

BIODEGRADABLE CATIONIC POLYMERS AND USES THEREOF

CROSS-REFERENCE TO RELATED APPLICATIONS

This application is a National Stage filing under 35 U.S.C. § 371 of International Application No. PCT/US2017/021888, filed Mar. 10, 2017, and claims the right of priority under 35 U.S.C. § 119 to U.S. Provisional Application No. 62/310,320, filed Mar. 18, 2016 and to U.S. Provisional Application No. 62/307,322 filed Mar. 11, 2016, which disclosures are herein incorporated by reference in their entirety.

BACKGROUND OF THE INVENTION

Gene therapy has received significant attention due to its potential application in replacement of faulty genes and treatment of various incurable diseases (References 1 and 2). Viral vectors like adenoviruses and retroviruses (References 3 and 4) may provoke mutagenesis and carcinogenesis (Reference 3). A variety of lipids, natural and synthetic cationic polymers have been used for modeling non-viral delivery systems (References 5-7), which have several advantages including safety, stability, large DNA and RNA loading capacity, and easy production (References 8 and 9).

The success of gene therapy largely depends on delivery vehicles itself. Such cationic gene delivery polymers like poly(ethylenimine) (PEI), poly(2-dimethylaminoethyl methacrylate), and poly-L-lysine (References 10-15) have good transfection properties, both in vitro and in vivo. Unfortunately, there are a large number of problems associated with the use of these vectors (References 16-18). The currently available cationic polymers, however, are toxic, mostly due to their poor biocompatibility and nondegradability under physiological conditions. Consequently, the development of hydrolyzable cationic polymers was proposed, such as poly(β-amino ester)s (References 19-21), poly(amino ester)s (References 22 and 23), and poly(amido amine)s (References 24 and 25).

Accordingly, the development of new cationic polymers, such as the poly(hydroxylalkyleneimine disulfide)s disclosed herein, that have both desirable transfection properties and reduced toxicity is of interest and utility.

BRIEF SUMMARY OF THE INVENTION

Herein are provided, inter alia, cationic polymers and methods of using the same.

In an aspect is provided a cationic polymer that is a poly(hydroxylalkyleneimine disulfide). In embodiments, said cationic polymer results from the polymerization of:
(a) a 1,ω-dibromoalkyl monomer; and
(b) a ω,ω'-diaminoalkyl disulfide monomer, and optionally;
(c) a 1,ω-diaminoalkyl monomer.

In an aspect is provided a composition comprising
(a) a cationic polymer that is a poly(hydroxylalkyleneimine disulfide), or a salt thereof; and
(b) at least one nucleic acid.

In an aspect is provided a method of delivering at least one nucleic acid to a cell comprising contacting a cell with a composition described herein.

In an aspect is provide an agent suitable for delivering at least one nucleic acid to a cell where the agent comprises a composition described herein.

In an aspect is provided a pharmaceutical product comprising a composition as described herein.

BRIEF DESCRIPTION OF THE DRAWINGS

FIG. 7A shows before DTT treatment, and FIG. 7B shows after DTT treatment.

FIG. 8A shows transfection efficiency, and FIG. 8B shows RNA levels from the same samples.

DETAILED DESCRIPTION OF THE INVENTION

I. Definitions

Figure 1:
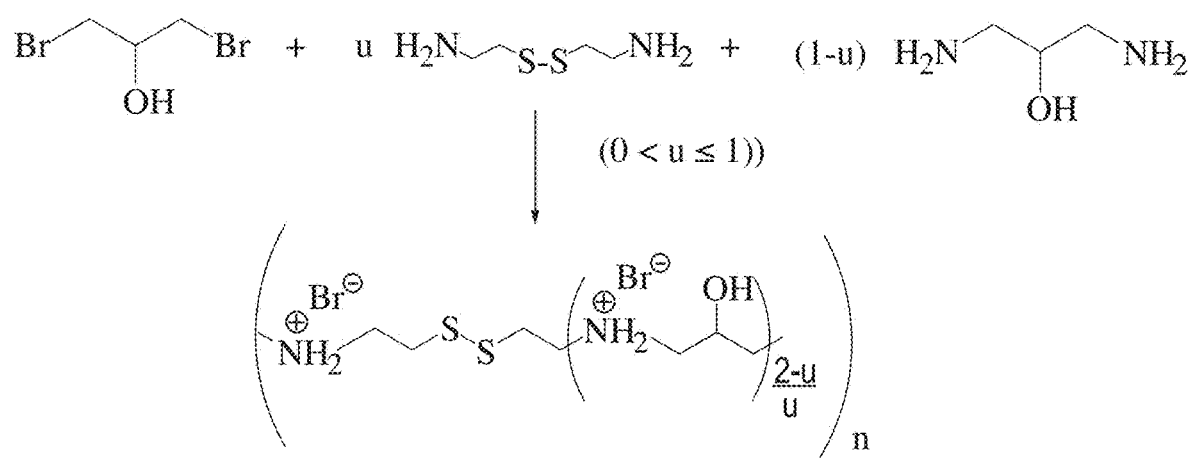
FIG. 1 provides an exemplary, simplified scheme of polycondensation between DAP, CT and DBP, where the relative molar equivalents of CT and DAP are indicated relative to DBP, and where [CT+DAP]=[DBP].

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl" by itself or as part of another substituent means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, B, As, and Si may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SW, and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The term "1,ω-dibromoalkyl monomer" is used in accordance with its plain ordinary meaning in the art and, as such, refers to an alkyl compound wherein each terminal carbon comprises a substituent group that is —Br. The 1,ω-dibromoalkyl monomer may be branched or unbranched (straight). In embodiments, a 1,ω-dibromoalkyl monomer does not comprise any further substituents: such a difunctionalized compound may also be referred to as an "unsubstituted 1,ω-dibromoalkyl monomer." In embodiments, a 1,ω-dibromoalkyl monomer comprises further substituents (e.g., those described herein for alkyls and alkyl radicals): such a polyfunctionalized compound may also be referred to as a "substituted 1,ω-dibromoalkyl monomer." Exemplary substituents include —OH substituents ("hydroxy" or "hydroxyl"). In embodiments, a substituted 1,ω-dibromoalkyl monomer comprises 1, 2, 3, 4, 5, or 6 further substituents. In embodiments, a 1,ω-dibromoalkyl monomer comprises one —OH substituent.

The term "ω,ω'-diaminoalkyl disulfide monomer" is used in accordance with its plain ordinary meaning in the art and, as such, refers to a heteroalkyl compound wherein each terminal carbon comprises a substituent group that is —NH$_2$, and wherein the straight or branched chain comprises a disulfide (—S—S—) moiety. In embodiments, a ω,ω'-diaminoalkyl disulfide monomer does not comprise any further substituents: such a compound may also be referred to as an "unsubstituted ω,ω'-diaminoalkyl disulfide monomer." In embodiments, a ω,ω'-diaminoalkyl disulfide monomer comprises further substituents (e.g., those described herein for heteroalkyls and heteroalkyl radicals): such a compound may also be referred to as a "substituted ω,ω'-diaminoalkyl disulfide monomer." In embodiments, a substituted ω,ω'-diaminoalkyl disulfide monomer comprises 1, 2, 3, 4, 5, or 6 further substituents.

The term "1,ω-diaminoalkyl monomer" is used in accordance with its plain ordinary meaning in the art and, as such, refers to an alkyl compound wherein each terminal carbon comprises a substituent group that is —NH$_2$. The 1,ω-diaminoalkyl monomer may be branched or unbranched (straight). In embodiments, a 1,ω-diaminoalkyl monomer does not comprise any further substituents: such a difunctionalized compound may also be referred to as an "unsubstituted 1,ω-diaminoalkyl monomer." In embodiments, a 1,ω-diaminoalkyl monomer comprises further substituents (e.g., those described herein for alkyls and alkyl radicals): such a polyfunctionalized compound may also be referred to as a "substituted 1,ω-diaminoalkyl monomer." Exemplary substituents include —OH substituents ("hydroxyl" or "hydroxyl"). In embodiments, a substituted 1,ω-diaminoalkyl monomer comprises 1, 2, 3, 4, 5, or 6 further substituents. In embodiments, a 1,ω-diaminoalkyl monomer comprises one —OH substituent.

The symbol "$\sim\!\sim\!\sim$" denotes the point of attachment of a chemical moiety to the remainder of a molecule or chemical formula.

Each of the above terms (e.g., "alkyl" and "heteroalkyl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R, —C(O)R', —CO$_2$R, —CONR'R", —OC(O)NR'R", —NR"C(O)R, —NR'—C(O)NR"R'", —NR"C(O)$_2$R', —NR—C(NR'R"R'")=NR"", —NR—C(NR'R")=NR'", N=C(NR'R")(NR'"R")), —S(O)R, —S(O)$_2$R', —S(O)$_2$NR'R", —NRSO$_2$R', —NR'NR"R'", ONR'R", —NRC(O)NR"NR"'R", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R'', R''', and R'''' group when more than one of these groups is present. When R' and R'' are attached to the same nitrogen atom, they can be combined with the nitrogen atom to form a 4-, 5-, 6-, or 7-membered ring. For example, —NR'R'' includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:
(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, heteroaryl, substituted with at least one substituent selected from:
  (i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
    (a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), phosphorus 32 ($^{32}$P) or carbon-14 ($^{14}$C). All isotopic variations of the compounds of the present invention, whether radioactive or not, are encompassed within the scope of the present invention.

It should be noted that throughout the application that alternatives are written in Markush groups. It is specifically contemplated that each member of the Markush group should be considered separately, thereby comprising another embodiment, and the Markush group is not to be read as a single unit.

The terms "a" or "an," as used in herein means one or more. In addition, the phrase "substituted with a[n]," as used herein, means the specified group may be substituted with one or more of any or all of the named substituents. For example, where a group, such as an alkyl or heteroalkyl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A salt of any compound described herein is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The term "individual" refers to a mammal, including humans. An individual includes, but is not limited to, human, bovine, horse, feline, canine, rodent, or primate. In some embodiments, the individual is human. In some embodiments, the individual is a human.

Unless indicated otherwise, the term "about" in the context of a numeric value indicated the nominal value±10% of the nominal value. Reference to "about" a value or parameter herein includes (and describes) embodiments that are directed to that value or parameter per se. For example, description referring to "about X" includes description of X.

The word "transfect" is broadly used herein to refer to introduction of an exogenous compound, such as a nucleic acid, into a prokaryotic or eukaryotic cell; the term includes, without limitation, introduction of an exogenous nucleic acid into a cell, which may result in a permanent or temporary alteration of genotype in an immortal or non-immortal cell line. Accordingly, embodiments of the present disclosure include the introduction of a polynucleotide sequence to either be expressed or to inhibit expression of a target gene.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of cancer antigens. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

II. Compounds

In an aspect is provided a cationic polymer that is a poly(hydroxylalkyleneimine disulfide).

In embodiments, the cationic polymer results from the polymerization of:
(a) a 1,ω-dibromoalkyl monomer; and
(b) a ω,ω'-diaminoalkyl disulfide monomer, and optionally;
(c) a 1,ω-diaminoalkyl monomer.

In embodiments, the cationic polymer results from the polymerization of
(a) a 1,ω-dibromoalkyl monomer; and
(b) a ω,ω'-diaminoalkyl disulfide monomer, and
(c) a 1,ω-diaminoalkyl monomer.

In embodiments, said 1,ω-dibromoalkyl monomer is

$L^{M1}$ is independently substituted or unsubstituted alkylene.

In embodiments, said 1,ω-dibromoalkyl monomer (M1) is Br—$(CH_2)_m$—(CHOH)—$(CH_2)_{m'}$—Br, wherein m and m' are, independently, an integer of 1 to 10 (e.g., m is independently 1, 2, 3, 4, 5, 6, 7, 8, 9, or 10, and m' is independently 1, 2, 3, 4, 5, 6, 7, 8, 9, or 10). In embodiments, m and m' are each independently 1, 2, 3, 4, 5, or 6. In embodiments, m and m' are each independently 1 or 2. In embodiments, M1 is 1,3-dibromo-2-propanol (DBP).

In embodiments, said 1,ω-dibromoalkyl monomer (M1) is Br—$(CH_2)_{m''}$—Br, wherein m" is an integer of 1 to 20 (e.g., m" is 1, 2, 3, 4, 5, 6, 7, 8, 9, 10, 11, 12, 13, 14, 15, 16, 17, 18, 19 or 20). In embodiments, m" is 1, 2, 3, or 4.

In embodiments, said ω,ω'-diaminoalkyl disulfide monomer is

$L^{M2A}$ and $L^{M2B}$ are independently substituted or unsubstituted alkylene.

In embodiments, said ω,ω'-diaminoalkyl disulfide monomer (M2) is $H_2N$—$(CH_2)_{11}$—S—S—$(CH_2)_{n'}$—$NH_2$, wherein n and n' are, independently, an integer of 2 to 10 (e.g., n is independently 2, 3, 4, 5, 6, 7, 8, 9, or 10, and n' is independently 2, 3, 4, 5, 6, 7, 8, 9, or 10). In embodiments, n and n' are each independently 2, 3, 4, 5, or 6. In embodiments, n and n' are each independently 2, 3, or 4. In embodiments, M2 is cystamine (CT).

In embodiments, said 1,ω-diaminoalkyl monomer, when present, is

$L^{M1}$ is independently substituted or unsubstituted alkylene.

In embodiments, said 1,ω-diaminoalkyl monomer (M3) is $H_2N$—$(CH_2)_m$—(CHOH)—$(CH_2)_{m'}$—$NH_2$, wherein m and m' are, independently, an integer of 1 to 10 (e.g., m and m' are independently 1, 2, 3, 4, 5, 6, 7, 8, 9, or 10). In embodiments, m and m' are each 1, 2, 3, 4, 5, or 6. In embodiments, m and m' are each 1 or 2. In embodiments, M3 is 1,3-diamino-2-propanol (DAP).

In embodiments, said 1,ω-diaminoalkyl monomer (M3) is $H_2N$—$(CH_2)_{m''}$—$NH_2$, wherein m" is an integer of 1 to 20 (e.g., m" is 1, 2, 3, 4, 5, 6, 7, 8, 9, 10, 11, 12, 13, 14, 15, 16, 17, 18, 19 or 20). In embodiments, m" is 1, 2, 3, or 4.

In embodiments, the ratio of the 1,ω-dibromoalkyl monomer:ω,ω'-diaminoalkyl disulfide monomer:1,ω-diaminoalkyl monomer is about: 1:1:0; 1:0.9:0.1; 1:0.8:0.2; 1:0.75:0.25; 1:0.7:0.3; 1:0.6:0.4; 1:0.5:0.5; 1:0.4:0.6; 1:0.3:0.7; 1:0.25:0.75; 1:0.2:0.8; or 1:0.1:0.9.

In embodiments, the ω,ω'-diaminoalkyl disulfide monomer is cystamine (CT).

In embodiments, the 1,ω-dibromoalkyl monomer is substituted with a hydroxyl group.

In embodiments, the 1,ω-dibromoalkyl monomer is 1,3-dibromo-2-propanol (DBP).

In embodiments, the 1,ω-diaminoalkyl monomer is substituted with a hydroxyl group.

In embodiments, the 1,ω-diaminoalkyl monomer is 1,3-diamino-2-propanol (DAP).

In embodiments, the cationic polymer results from the polymerization of
(a) 1,3-dibromo-2-propanol (DBP); and
(b) cystamine (CT).

In embodiments, the ratio of DBP:CT is about: 1:1; 0.9:0.1; 0.8:0.2; 0.7:0.3; 0.6:0.4; 0.4:0.6; 0.7:0.3; 0.8:0.2; or 0.9:0.1. In embodiments, the ratio of DBP:CT is about 1:1.

In embodiments, the cationic polymer results from the polymerization of
(a) 1,3-dibromo-2-propanol (DBP);
(b) cystamine (CT); and
(c) 1,3-diamino-2-propanol (DAP).

In embodiments, the ratio of DBP:CT:DAP is about: 1:0.9:0.1; 1:0.8:0.2; 1:0.75:0.25; 1:0.7:0.3; 1:0.6:0.4; 1:0.5:0.5; 1:0.4:0.6; 1:0.3:0.7; 1:0.25:0.75; 1:0.2:0.8; or 1:0.1:0.9. In embodiments, the ratio of DBP:CT:DAP is about 1:0.7:0.3 or 1:0.5:0.5.

In embodiments, the cationic polymer is linear.
In embodiments, the cationic polymer is branched.

In embodiments, the cationic polymer has a repeating unit that is,

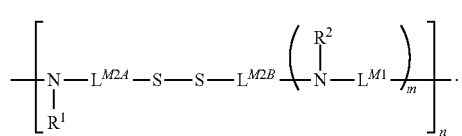

m is an integer of 1 to 20 (e.g., 1, 2, 3, 4, 5, 6, 7, 8, 9, 10, 11, 12, 13, 14, 15, 16, 17, 18, 19, or 20).
n is an integer of 2 to 150 (e.g., 2 to 100).
Each $R^1$ and $R^2$ is independently hydrogen or substituted or unsubstituted heteroalkyl.
Each $L^{M2A}$ and $L^{M2B}$ is independently substituted or unsubstituted alkylene.
$L^{M1}$ is independently hydroxyl-substituted alkylene.

In embodiments, the cationic polymer is represented by the following formula,

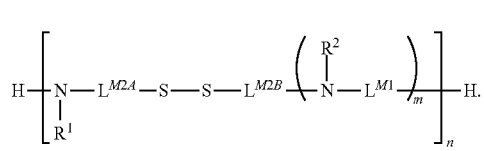

In embodiments, the cationic polymer has a repeating unit that is

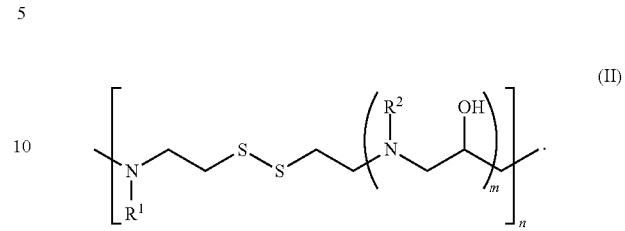

In embodiments, the cationic polymer is represented by the following formula,

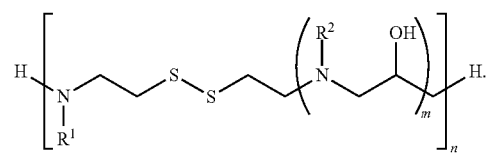

In embodiments, each $R^1$ and $R^2$ is independently hydrogen or a heteroalkyl of substructure (A) or substructure (B).

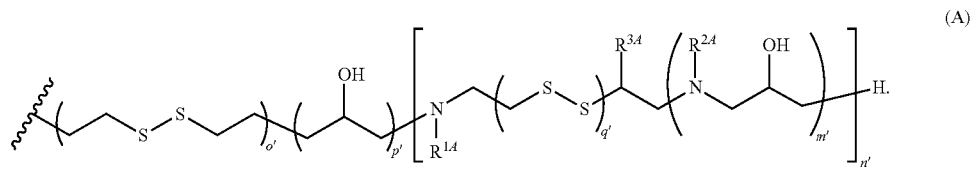

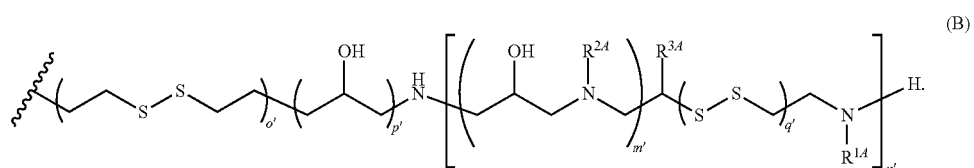

o' is 0 or 1.

p' is 0 or 1.

o'+p'=1.

q' is 0 or 1.

When q' is 0, $R^{3A}$ is OH; and when q' is 1, $R^{3A}$ is hydrogen.

m' is an integer of 1 to 20 (e.g., m'1 is 1, 2, 3, 4, 5, 6, 7, 8, 9, 10, 11, 12, 13, 14, 15, 16, 17, 18, 19, or 20.).

n' is an integer of 2 to 100 (e.g., an integer of 2 to 50).

Each $R^{1A}$ and $R^{2A}$ is independently hydrogen or substituted or unsubstituted heteroalkyl.

In embodiments, at least one of $R^1$ and $R^2$ is a substituted or unsubstituted heteroalkyl.

In embodiments, o' is 0, and p' is 1. In embodiments, o' is 1, and p' is 0.

In embodiments, q' is 0.

In embodiments, q' is 1, and $R^{3A}$ is hydrogen.

In embodiments, the cationic polymer of formula (I) results from the polymerization of
 (a) 1,3-dibromo-2-propanol (DBP);
 (b) cystamine (CT), and optionally;
 (c) 1,3-diamino-2-propanol (DAP).

In an aspect is provided a composition comprising
 (a) a cationic polymer that is a poly(hydroxylalkylene-imine disulfide), or a salt thereof; and
 (b) at least one nucleic acid.

In embodiments, the ratio of DBP:CT:DAP is about: 1:1:0; 1:0.9:0.1; 1:0.8:0.2; 1:0.75:0.25; 1:0.7:0.3; 1:0.6:0.4; 1:0.5:0.5; 1:0.4:0.6; 1:0.3:0.7; 1:0.25:0.75; 1:0.2:0.8; or 1:0.1:0.9. In embodiments, the ratio of DBP:CT:DAP is about 1:1:0; 1:0.7:0.3 or 1:0.5:0.5.

In embodiments, the weight average molecular weight ($M_w$) is between about 4,000 and about 20,000 (e.g., between about 4,000 and about 10,000). In embodiments, the weight average molecular weight ($M_w$) is about 4,000; 5,000; 6,000; 7,000; 8,000; 9,000; 10,000; 12,000; 14,000; 16,000; 18,000; or 20,000. In embodiments, the weight average molecular weight ($M_w$) is about 4,000; 5,000; 6,000; 7,000; 8,000; 9,000 or 10,000.

In embodiments, each $L^{M1}$ is independently substituted alkylene. In embodiments, each $L^{M1}$ is independently unsubstituted alkylene. In embodiments, each $L^{M1}$ is independently substituted or unsubstituted $C_1$-$C_6$ alkylene. In embodiments, each $L^{M1}$ is independently substituted $C_1$-$C_6$ alkylene. In embodiments, each $L^{M1}$ is independently unsubstituted $C_1$-$C_6$ alkylene.

In embodiments, each $L^{M1}$ is independently $R^4$-substituted or unsubstituted alkylene.

In embodiments, $R^4$ is independently hydrogen, oxo, $-CX^4_3$, $-CHX^4_2$, $-CH_2X^4$, $-OCX^4_3$, $-OCHX^4_2$, $-OCH_2X^4$, halogen, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^5$-substituted or unsubstituted alkyl, $R^5$-substituted or unsubstituted heteroalkyl, $R^5$-substituted or unsubstituted cycloalkyl, $R^5$-substituted or unsubstituted heterocycloalkyl, $R^5$-substituted or unsubstituted aryl, or $R^5$-substituted or unsubstituted heteroaryl. $X^4$ is halogen. In embodiments, $X^4$ is F. In embodiments, $R^4$ is $-OH$.

In embodiments, each $L^{M2A}$ is independently substituted alkylene. In embodiments, each $L^{M2A}$ is independently unsubstituted alkylene. In embodiments, each $L^{M2A}$ is independently substituted or unsubstituted $C_1$-$C_6$ alkylene. In embodiments, each $L^{M2A}$ is independently substituted $C_1$-$C_6$ alkylene. In embodiments, each $L^{M2A}$ is independently unsubstituted $C_1$-$C_6$ alkylene.

In embodiments, each $L^{M2A}$ is independently $R^6$-substituted or unsubstituted alkylene.

In embodiments, $R^6$ is independently hydrogen, oxo, $-CX^6_3$, $-CHX^6_2$, $-CH_2X^6$, $-OCX^6_3$, $-OCHX^6_2$, $-OCH_2X^6$, halogen, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^7$-substituted or unsubstituted alkyl, $R^7$-substituted or unsubstituted heteroalkyl, $R^7$-substituted or unsubstituted cycloalkyl, $R^7$-substituted or unsubstituted heterocycloalkyl, $R^7$-substituted or unsubstituted aryl, or $R^7$-substituted or unsubstituted heteroaryl. $X^6$ is halogen. In embodiments, $X^6$ is F. In embodiments, $R^6$ is $-OH$.

In embodiments, each $L^{M2B}$ is independently substituted alkylene. In embodiments, each $L^{M2B}$ is independently unsubstituted alkylene. In embodiments, each $L^{M2B}$ is independently substituted or unsubstituted $C_1$-$C_6$ alkylene. In embodiments, each $L^{M2B}$ is independently substituted $C_1$-$C_6$ alkylene. In embodiments, each $L^{M2B}$ is independently unsubstituted $C_1$-$C_6$ alkylene.

In embodiments, each $L^{M2B}$ is independently $R^8$-substituted or unsubstituted alkylene.

In embodiments, $R^8$ is independently hydrogen, oxo, $-CX^8_3$, $-CHX^8_2$, $-CH_2X^8$, $-OCX^8_3$, $-OCHX^8_2$, $-OCH_2X^8$, halogen, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^9$-substituted or unsubstituted alkyl, $R^9$-substituted or unsubstituted heteroalkyl, $R^9$-substituted or unsubstituted cycloalkyl, $R^9$-substituted or unsubstituted heterocycloalkyl, $R^9$-substituted or unsubstituted aryl, or $R^9$-substituted or unsubstituted heteroaryl. $X^8$ is halogen. In embodiments, $X^8$ is F. In embodiments, $R^8$ is $-OH$.

In embodiments, each $R^1$ is independently hydrogen. In embodiments, each $R^1$ is independently substituted or unsubstituted heteroalkyl. In embodiments, each $R^1$ is independently substituted heteroalkyl. In embodiments, each $R^1$ is independently unsubstituted heteroalkyl. In embodiments, $R^1$ is independently substituted or unsubstituted 2 to 6 membered heteroalkyl. In embodiments, $R^1$ is independently substituted 2 to 6 membered heteroalkyl. In embodiments, $R^1$ is independently unsubstituted 2 to 6 membered heteroalkyl.

In embodiments, each $R^1$ is independently hydrogen or $R^{10}$-substituted or unsubstituted heteroalkyl.

In embodiments, $R^{10}$ is independently hydrogen, oxo, $-CX^{10}_3$, $-CHX^{10}_2$, $-CH_2X^{10}$, $-OCX^{10}_3$, $-OCHX^{10}_2$, $-OCH_2X^{10}$, halogen, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, R"-substituted or unsubstituted alkyl, R"-substituted or unsubstituted heteroalkyl, R"-substituted or unsubstituted cycloalkyl, R"-substituted or unsubstituted heterocycloalkyl, R"-substituted or unsubstituted aryl, or R"-substituted or unsubstituted heteroaryl. $X^{10}$ is halogen. In embodiments, $X^{10}$ is F. In embodiments, $R^{10}$ is $-OH$.

In embodiments, each $R^1$ is independently substructure (A). In embodiments, each $R^1$ is independently substructure (B).

In embodiments, each $R^2$ is independently hydrogen. In embodiments, each $R^2$ is independently substituted or unsubstituted heteroalkyl. In embodiments, each $R^2$ is independently substituted heteroalkyl. In embodiments, each $R^2$ is independently unsubstituted heteroalkyl. In embodiments, $R^2$ is independently substituted or unsubstituted 2 to 6 membered heteroalkyl. In embodiments, $R^2$ is independently substituted 2 to 6 membered heteroalkyl. In embodiments, $R^2$ is independently unsubstituted 2 to 6 membered heteroalkyl.

In embodiments, each $R^2$ is independently hydrogen or $R^{12}$-substituted or unsubstituted heteroalkyl.

In embodiments, $R^{12}$ is independently hydrogen, oxo, —$CX^{12}_3$, —$CHX^{12}_2$, —$CH_2X^{12}$, —$OCX^{12}_3$, —$OCHX^{12}_2$, —$OCH_2X^{12}$, halogen, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{13}$-substituted or unsubstituted alkyl, $R^{13}$-substituted or unsubstituted heteroalkyl, $R^{13}$-substituted or unsubstituted cycloalkyl, $R^{13}$-substituted or unsubstituted heterocycloalkyl, $R^{13}$-substituted or unsubstituted aryl, or $R^{13}$-substituted or unsubstituted heteroaryl. $X^{12}$ is halogen. In embodiments, $X^{12}$ is F. In embodiments, $R^{12}$ is —OH.

In embodiments, each $R^2$ is independently substructure (A). In embodiments, each $R^2$ is independently substructure (B).

In embodiments, each $R^{1.4}$ is independently hydrogen. In embodiments, each $R^{1.4}$ is independently substituted or unsubstituted heteroalkyl. In embodiments, each $R^{1.4}$ is independently substituted heteroalkyl. In embodiments, each $R^{1.4}$ is independently unsubstituted heteroalkyl. In embodiments, $R^{1.4}$ is independently substituted or unsubstituted 2 to 6 membered heteroalkyl. In embodiments, $R^{1.4}$ is independently substituted 2 to 6 membered heteroalkyl. In embodiments, $R^{1.4}$ is independently unsubstituted 2 to 6 membered heteroalkyl.

In embodiments, each $R^{1.4}$ is independently hydrogen or $R^{14}$-substituted or unsubstituted heteroalkyl.

In embodiments, $R^{14}$ is independently hydrogen, oxo, —$CX^{14}_3$, —$CHX^{14}_2$, —$CH_2X^{14}$, —$OCX^{14}_3$, —$OCHX^{14}_2$, —$OCH_2X^{14}$, halogen, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{15}$-substituted or unsubstituted alkyl, $R^{15}$-substituted or unsubstituted heteroalkyl, $R^{15}$-substituted or unsubstituted cycloalkyl, $R^{15}$-substituted or unsubstituted heterocycloalkyl, $R^{15}$-substituted or unsubstituted aryl, or $R^{15}$-substituted or unsubstituted heteroaryl. $X^{14}$ is halogen. In embodiments, $X^{14}$ is F. In embodiments, $R^{14}$ is —OH.

In embodiments, each $R^{2.4}$ is independently hydrogen. In embodiments, each $R^{2.4}$ is independently substituted or unsubstituted heteroalkyl. In embodiments, each $R^{2.4}$ is independently substituted heteroalkyl. In embodiments, each $R^{2.4}$ is independently unsubstituted heteroalkyl. In embodiments, $R^{2.4}$ is independently substituted or unsubstituted 2 to 6 membered heteroalkyl. In embodiments, $R^{2.4}$ is independently substituted 2 to 6 membered heteroalkyl. In embodiments, $R^{2.4}$ is independently unsubstituted 2 to 6 membered heteroalkyl.

In embodiments, each $R^{2.4}$ is independently hydrogen or $R^{16}$-substituted or unsubstituted heteroalkyl.

In embodiments, $R^{16}$ is independently hydrogen, oxo, —$CX^{16}_3$, —$CHX^{16}_2$, —$CH_2X^{16}$, —$OCX^{16}_3$, —$OCHX^{16}_2$, —$OCH_2X^{16}$, halogen, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{17}$-substituted or unsubstituted alkyl, $R^{{\prime}7}$-substituted or unsubstituted heteroalkyl, $R^{17}$-substituted or unsubstituted cycloalkyl, $R^{{\prime}7}$-substituted or unsubstituted heterocycloalkyl, $R^{17}$-substituted or unsubstituted aryl, or $R^{{\prime}7}$-substituted or unsubstituted heteroaryl. $X^{16}$ is halogen. In embodiments, $X^{16}$ is F. In embodiments, $R^{16}$ is —OH.

$R^5$, $R^7$, $R^9$, $R^{11}$, $R^{13}$, $R^{15}$, and $R^{17}$ are independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In an aspect is provided a composition comprising
(a) a cationic polymer that is a poly(hydroxylalkyleneimine disulfide), or a salt thereof; and
(b) at least one nucleic acid.

In embodiments, the composition further comprises one or more adjuvants. The one or more adjuvants may comprise a lipid, protein, lipopolyamine, or synthetic polymer.

In an aspect is provided a method of delivering at least one nucleic acid to a cell, said method comprising contacting a cell with a composition as described herein.

In embodiments, the method is carried out in vivo.

In embodiments, the method is carried out in vitro. In embodiments, the cell is comprised in a cultured cell line.

In an aspect is provided an agent suitable for delivering at least one nucleic acid to a cell comprising a composition as described herein.

In embodiments, a nucleic acid is a DNA or RNA. In embodiments, a DNA is doubled stranded (dsDNA). In embodiments, a DNA is single stranded (ssDNA). In embodiments, an RNA is double stranded (dsRNA). In embodiments, an RNA is single stranded (ssRNA).

In embodiments, a nucleic acid is a DNA (e.g., a plasmid DNA, a deoxyribozyme,).

In embodiments, a nucleic acid is an RNA (e.g., a ribozyme, a short interfering RNA (siRNA), a short hairpin RNA (shRNA), a micro RNA (miRNA), a piwi-interacting RNA (piRNA), an RNA-induced silencing complex (RISC), or a locked nucleic acid (LNA)). In embodiments, an siRNA is a chemically modified siRNA.

In embodiments, a nucleic acid is an antisense nucleic acid.

In embodiments, a nucleic acid is an aptamer.

In an aspect is provided a pharmaceutical product comprising a composition as described herein.

III. Compositions and Methods of Use

Disulfide (—S—S—) linked polymers (e.g., the cationic polymers described herein) form a class of polymers that can be used for gene delivery: they are stable in extracellular oxidizing milieu but easily degradable in the highly reductive intracellular medium (References 28 and 29). Successful intracellular destruction of the complexes consequently facilitates the release DNA/siRNA and increases the gene expression (Reference 30).

Disulfide linked polymers have several advantages. For example, —S—S— bonds are more hydrolytically stable than ester bonds in the extracellular environment, so the polycations with disulfide bonds can be used to prepare stable complexes with plasmid DNA or siRNA. Moreover, disulfide bonds can be cleaved rapidly by glutathione and thioredoxin reductases in cytoplasm, and cytotoxicity will be decreased by avoiding high charge density and long-term polymer accumulation. Accordingly, disulfide bonds are useful in the design and synthesis of biodegradable polymers including gene delivery vehicles (Reference 26 and 27).

The design of degradable polycationic gene carriers such as the reducible disulfide-containing poly(amidoamine)s (SS-PAA)s and poly(ethylenimine)s have demonstrated comparable or improved cellular gene delivery and less cell toxicity when compared to PEIs (e.g., the cationic polymers described herein). A bioreducible (SS-PAA)s showed promising properties for gene delivery, combining efficient transfection with low cytotoxicity profiles. These polymers could be easily synthesized by the Michael addition reaction of the disulfide-containing cystamine bisacrylamide (CBA) with various primary amines, thereby allowing large structural variation of the side groups in the amine moiety (Reference 28, 29 and 30). Lin and Engbersen investigated synthesis of linear and branched poly(amido amine)s and their structural effects on effective gene transfection (Reference 29). They synthesized poly (amido-ethylenimines) of cystamine bisacrylamide (CBA) with three different ethylenediamine, diethylenetriamine and triethylenetetramine. These copolymers containing three disulfide linkages exhibited 20-fold higher transfection activity compared to branched PEI 25 kDa in various cell lines, including NIH3T3, endothelial and smooth muscle cells.

Low-molecular weight branched PEIs have been typically employed for designing redox-sensitive carriers because of their acceptable biocompatibility and structural composition analogous to 25 kDa branched PEI, an effective non-viral carrier. In vitro transfection efficiency of 800 Da branched PEI was shown to increase significantly as a result of —S—S— linking of the polymer via DMSO-mediated oxidation of thiol end-capped groups (Reference 31). Other crosslinkers, such as dithiobis(succinimidylpropionate) (DSP), dimethyl 3,3-dithiobispropionimidate (DTBP), bis (2-methacryloyloxyethyl) disulfide and cystamine bisacrylamide (CBA), were also employed to create disulfide-linked branched PEIs to enhance the transgene expression (References 32 and 33). Cross-linking of 800 Da branched PEI with CBA made its transfection efficiency comparable to PEI25, with marginal toxicity (Reference 34). The DSP-linked 800 Da PEI was superior to the DTBP-linked polymers in transfecting CHO cells, indicating the direct impact of the linker moiety to transfection outcome (Reference 34). Consequently, there is a need for biodegradable gene delivery polymers. The potential advantages of biodegradable carriers include their reduced toxicity and avoidance of accumulation of the polymer in the cells.

Recently, a new class of gene delivery vehicles—poly(2-hydroxyalkylene imines) were synthesized [Reference 35. These cationic polymers, possessing both imine and hydroxyl groups in their repeating units, showed no significant effect on the tested cell viability with the excellent gene delivery capability comparable or even better than commercially available transfection reagents Exgen500, Lipofectamine, Effectene and others. Unfortunately, at higher concentrations PHPI showed substantial cytotoxicity. Expecting substantial reduction of cytotoxicity of PHPI, we have synthesized a series of poly(2-hydroxypropylene imines) containing segments of cystamine (PHPI-SS). This new class of hydrophilic, cationic and disulfide bonds containing polymers were used as a carrier for the triggered intracellular release and activation of DNA/siRNA. The relationship between efficient intracellular unpacking of PHPI-SS complexes and enhanced DNA activity was investigated.

IV. Examples

General Experimentals

Materials

Cystamine dihydrochloride (98%), 1,3-diamino-2-propanol (DAP, 98%), 1,3-dibromo-2-propanol (DBP, 95%) and N,N-dimethylacetamide (DMAC, 99%) were purchased from Sigma-Aldrich. N,N-dimethylformamide (DMF, 99.8%), methanol (MeOH, 99.5%) and 2-propanol (IPOH, 99.7%) were obtained from Reachem Slovakia. Prior to use, all solvents were purified according to standard procedures and stored over molecular sieves (3 Å). Dubelcco's Modified Eagle's Medium (DMEM), RPMI-1640 medium, Trypsin-EDTA, L-glutamine, gentamicin sulphate, doxycycline and 1,4-dithiothreitol (DTT) were purchased from Sigma Aldrich, Fetal bovine serum (FBS)—from GE Healthcare Life Sciences, HeLa cells—from ATCC (LGS Standards, UK). EGFP encoding vector was synthesized at GenScript USA Inc. PHPI. Other reagents used were of analytical grade.

Cystamine Free Base

Cystamine dihydrochloride (8.7 g, 0.038 mol) was dissolved in water (30 ml). The mixture was cooled in an ice bath to 0° C., and 15 ml 10 M NaOH was slowly added during 1 hour. Cystamine free base (CT) was extracted with 100 ml dichloromethane, and the organic layer was separated and dried with $Na_2SO_4$. Dichloromethane was then evaporated under vacuum resulting 4.3 g (yield 73.1%) of viscous slightly yellow CT. Before use, the product was additionally dried with $Na_2CO_3$ and stored at −20° C. $^1H$ NMR ($CDCl_3$), ppm (referenced according to solvent signal): 1.30 (4H, —$NH_2$); 2.58 (4H, —S—$CH_2$—$CH_2$—$NH_2$); 2.80 (4H, 5-$CH_2$—$CH_2$—$NH_2$). $^{13}C$ NMR ($CDCl_3$), ppm (referenced according to solvent signal): 39.56 (2C, S—$CH_2$—$CH_2$—$NH_2$); 41.29 (2CH, —S—$CH_2$—$CH_2$—$NH_2$).

Methods

Synthesis of Poly(2-Hydroxypropylene Imines) Containing Segments of Cystamine (PHPI-SS)

PHPI was synthesized by the method described before [Reference 36] Synthesis of PHPI-SS1: CT 2.57 g (16.6 mmol) and DMAC 9.9 mL were placed in a 25 ml capacity round-bottom reaction flask submerged in an oil bath. Under moderate stirring, the reaction mixture was slowly preheated to 80° C. Then, under vigorous stirring, DBP (3.62 g, 16.6 mmol) was added dropwise to the reaction mixture, and the polycondensation was carried out for 168 hours. The resulting solution was diluted with 0.15 M NaCl solution (100 mL) and ultrafiltrated through a Pellicon membrane (Millipore) with nominal cut-off 10 kDa against water. PHPI-SS as a solid polymer was isolated by freeze-drying.

The same procedures were employed using different molar ratios of DBP, DAP and CT in DMAC, DMF, MeOH, and IPOH. Syntheses in MeOH and IPOH were conducted at 50° C. and 35° C., respectively.

Characterization of Poly(2-Hydroxypropylene Imines) Containing Segments of Cystamine (PHPI-SS)

Before analysis, PHPI-SS was purified by ultrafiltration. $^1H$ and $^{13}C$-NMR spectra were recorded on a Brucker 400 Ascend™ 400 MHz spectrometer at 29° C. in $D_2O$. $^1H$ and $^{13}C$-NMR signals were referenced according to DOH and tetramethylsilane, respectively. For quantitative measurements, $^{13}$C-NMR spectra were recorded using inverse gated decoupling pulse sequences, sample weight was approx. 100 mg, and approx. 6000 scans were performed. Molar ratio between 2-hydroxypropyleneimine and ethylenedithioethyleneimine (EDEI) segments in PHPI-SS (HPI/EDEI) was calculated from $^1$H-NMR spectra comparing intensities of the signals of methyne protons of HPI (at 3.9-4.4 ppm) and methylene protons of EDEI (at 3.7-2.3 ppm). Analogous estimation was made from $^{13}$C-NMR, comparing intensities at 65.7 ppm corresponding to carbon associated to methyne group in HPI and 32 ppm and 33.5 ppm associated to the carbon with disulfide group in EDEI. Degree of branching (DB) of PHPI-SS, as a ratio of secondary to tertiary nitrogen ($N_2/N_3$), were calculated from $^{13}$C-NMR spectra (Reference 36.

Molecular characteristics of the polymers were determined by size-exclusion chromatography (SEC). SEC analysis was performed on a Viscotek TDAmax system equipped with a triple-detection array TDA305 consisting of refractive index detector, right-angle and low-angle light scattering detectors, and four-capillary bridge viscosity detector. The universal column was A6000M (Viscotek). The system was eluted with 250 mM acetate buffer of pH 4 at a 0.5 ml/min flow rate and temperature 30° C. Sample concentration was 0.5 mg/ml. OmniSEC software from Viscotek was used to collect and analyze the data.

Elemental analysis was done with Thermo Scientific™ FLASH 2000 CHNSO analyzer and was used for calculation of HPI/EDEI. Elemental analysis (average from three separate analysis) of PHPI-SS1(%): (C: 32.02, H: 6.83, N: 9.03, S: 20.94); PHPI-SS2(%): (C: 32.95, H: 7.25, N: 10.41, S: 13.64); PHPI-SS3(%): (C: 32.03, H: 7.54, N: 10.49, S: 9.47);

Amount of disulfide groups in PHPI-SS was determined according to [Reference 37] with minor changes, namely, for —S—S— reduction a solid $NaBH_4$ and $AlCl_3$ was not used thereto. Titration of unreduced PHPI-SS was also employed in order to ascertain the absence of free thiol groups in the polymers. Disulfide content was calculated as an average from two separate reductions-titrations.

DNA Polymer Complex Analysis by DLS.

DNA-polymer complexes (polyplexes) were prepared as follows: pMTCe-EGFP plasmid DNA (1 µg) was diluted in 100 µL of 0.15M NaCl; cationic polymers were deposited on the wall of the same Eppendorf tube and vortexed immediately for few seconds to ensure an even distribution of the material; the measurements were performed immediately (0 time point) after 20 min and 60 min to evaluate the stability of the complexes. Polyplex sizes were measured using dynamic light scattering device Malvern Zetasizer NanoS. Experimental data was analyzed using Malvern DTS v 5.10 software package.

Transfection.

One day before the experiment, HeLa cells were seeded in a 24-well tissue culture plate at the density of $6 \times 10^4$ cells per well in the total volume of 1 mL DMEM culture medium supplemented with 10% FBS, 2 mM L-glutamine and 2 mM gentamicine. The cells were incubated at 37° C. in a $CO_2$ incubator until they reached 70-80% confluency (usually within 24 h). Transfection complexes were prepared by diluting 0.5 µg of pMTCe-EGFP plasmid DNA in the serum-free medium; DNA-polymer mixtures were incubated for 15 min at room temperature and added to the cells in a dropwise manner. The final concentration of cationic polymers in the cell culture was 7.5 to 120 µM (based on N residues).

The transfection efficiency was evaluated 48 h later: cells were trypsinized, collected and mixed at 1:1 ratio with 2% paraformaldehyde/PBS solution. Fixed cells were analysed by flow cytometry using Guava EasyCyte8HT system and Guava CytoSoft 2.2.3 cell acquisition/analysis software (Millipore). Toxicity (the percent of dead cells) within the total population of analyzed cells was estimated based on forward and side scatter distribution—smaller and/or more granular cells were gated out. The percent of GFP$^+$ cells and mean fluorescence intensity (MFI) were evaluated within the population of viable cells.

Gel-Filtration Chromatography for PHPI-SS Polymer Degradation Studies.

Gel-filtration was performed using Amersham Biosciences Acta Purifier liquid chromatography system and Superdex 75 10/300 GL chromatography column with separation range for molecular weights between 3 000 and 70 000. Column volume was 24.5 ml, eluent 0.2 M NaCl, flow rate 0.5-1.0 ml/min, pressure maximum—1.8 MPa. Polymer sample (0.5 ml)±reducing agent DTT (final concentration 150 nM) was filtered through 0.22 µm filter and loaded onto the column. Polymer detection performed at 220 nm.

DNA Release from Polyplexes.

DNA shift in an agarose gel method was used to monitor polymer degradation and DNA release. All samples were prepared in duplicates. Reporter plasmid DNA (1 µg) was resuspended in 15 µl of 0.15 M NaCl, different amounts of biodegradable polymers were added so that final concentration ranged from 1 to 30 nM, reaction mixture was incubated for 15 min. DTT was added to half of the samples, the mix was incubated for 15 more minutes. DNA release (shift) was visualized in 1% agarose gel.

Double DNA Transfection and RNA Extraction.

One day before transfection cells were seeded in a 6-well tissue culture plate at the density $6 \times 10^4$ cells/ml in 4 ml of culture medium. Confluency of the cells on the day of transfection (24 h after seeding) reached 80%. DNA-polymer complexes were prepared in 400 µl of serum-free medium with 4 µg of plasmid and biodegradable polymer of selected concentration. Transfection complexes were added to half of the wells; 24 h later fresh polyplexes were prepared as described above and added to all wells. In the end, half of the cultures were transfected twice, and half were transfected once. After additional 24 hour incubation, all cells (transfected once or twice) were collected and resuspended in FACS buffer (1×PBS/2% FBS/0.1% Na azide). Cells were counted, $10^6$ cells from each sample were used for RNA extraction, the rest was used to determine the transfection efficiency by flow cytometry. RNA was purified using GeneJet™ RNA Purification Kit (Thermo Fisher Scientific), 10 µl of sample was stained with 2×RNA Loading dye and resolved on 1% agarose gel. Transfection efficiency was evaluated by flow cytometry as described earlier.

Example 1. Synthesis and Characterization of Poly(2-Hydroxypropylene Imines) Containing Segments of Cystamine PHPI-SS containing multiple biodegradable disulfide linkages in the main chain were synthesized by polycondensation of 1,3-diamino-2-propanol (DAP), 1,3-dibromo-2-propanol (DBP) and free cystamine base (CT), and FIG. 1 illustrates a representative synthesis. For example, in FIG. 1, "u" is any real number higher than zero and equal or less than one, and "n" represents the degree of polymerization. Accordingly, in this figure, the total amount of DAP and CT is equal to the amount of DBP. Synthesis was carried out in four different solvents, namely, methanol (MeOH), 2-propanol (IPOH), N,N-dimethylacetamide (DMAC) and N,N-dimethylformamide (DMF). Moreover, in order to vary amount of disulfide bonds, polycondensation was carried out at various ratios of CT, DAP and DBP.

Preliminary study has revealed that polycondensation in MeOH, IPOH and DMF at 35-60° C. resulted in PHPI-SS whose yield after ultrafiltration through 10 kDa cut-off membrane was less than 2%. The yield of PHPI-SS synthesized in DMAC at 80° C. was higher, over 7%. The present study deals with synthesis of PHPI-SS in DMAC at 80° C. The polymers were named as PHPI-SS1 to PHPI-SS3 (Table 1).

TABLE 1

Yield and molecular parameters of PHPI-SS purified by ultrafiltration

| Polymer | Ratio of the monomers | | | Yield,[a] % | $M_w$[b] | $M_w/M_n$[b] | $N_2/N_3$[c] |
|---|---|---|---|---|---|---|---|
| | DBP | CT | DAP | | | | |
| PHPI-SS1 | 1 | 1 | — | 4.5 | 4.2 | 1.98 | 1.76 |
| PHPI-SS2 | 1 | 0.7 | 0.3 | 1.4 | 3.9 | 1.52 | 1.65 |
| PHPI-SS3 | 1 | 0.5 | 0.5 | 4.8 | 7.9 | 1.56 | 2.01 |

[a] determined by gravimetric method;
[b] determined by SEC;
[c] determined by $^{13}$C NMR spectroscopy In order to remove low molecular weight fraction, fractionation was done by ultrafiltration using 10 kDa cut-off membrane. The molecular weight of polycondensates in all cases was low, and this resulted in low yields (1.4-4.8%) of the purified PHPI-SS. Weight average molecular weights ($M_w$) of PHPI-SS after ultrafiltration ranged from ~4.2 to 7.9 kDa with dispersity index at about 2 (Table 1).

Figure 2:
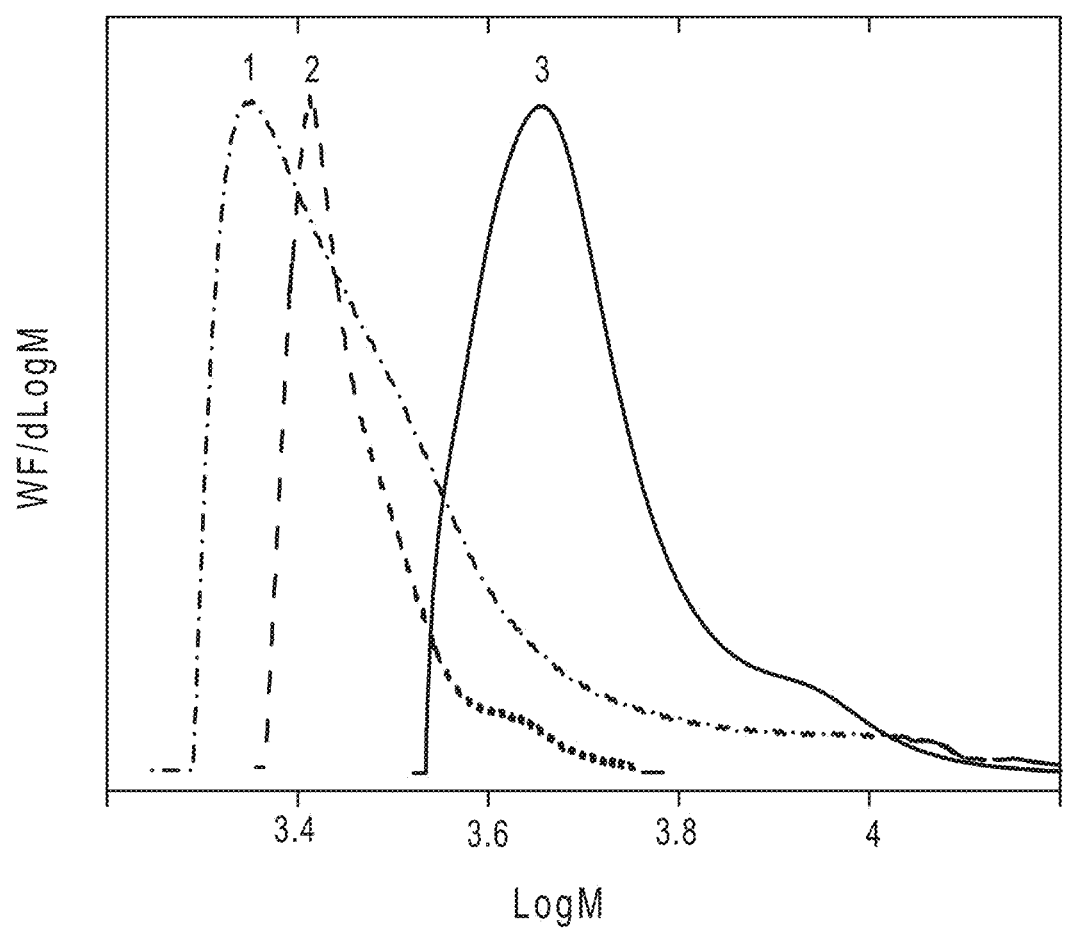
FIG. 2 provides MWD curves of the fractionated PHPI-SS1 (1), PHPI-SS2 (2) and PHPI-SS3 (3).

FIG. 2 provides MWD curves of the fractionated PHPI-SS1 (1), PHPI-SS2 (2), and PHPI-SS3 (3).

Weight average molecular weight of PHPI-SS1 and PHPI-SS2 are similar and close to 4000 while that of PHPI-SS3 containing the smallest amount of cystamine units is about twice higher. The curves of molecular weight distributions of the polymers (FIG. 2) have slightly expressed bimodality and high-molecular "tails". High molecular weight fraction of the polymers, possibly, is related to partial crosslinking of the polycondensates.

Figure 3:
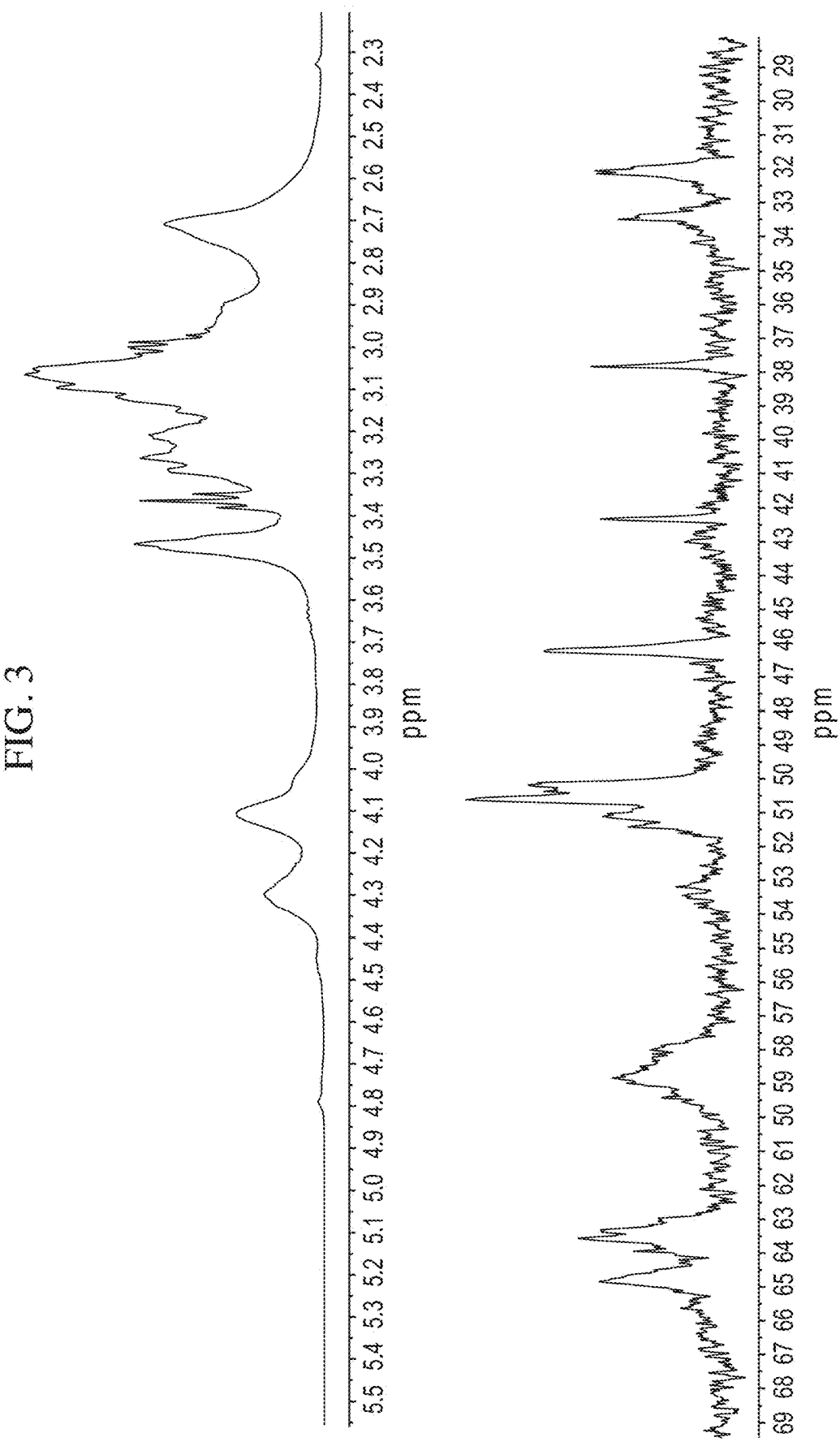
FIG. 3 provides $^1$H-NMR (top) and $^{13}$C-NMR (bottom) spectra of the fractionated PHPI-SS3.

Polymers were characterized by $^1$H and $^{13}$C-NMR spectroscopy. As an example, $^1$H-NMR spectrum of PHPI-SS3 in $D_2O$ (FIG. 3) contains a broad signal at 2.71-3.47 ppm attributed to (—CH$_2$—CH$_2$—S—S—CH$_2$—CH$_2$—NH—CH$_2$—CH(OH)—CH$_2$—), and two signals at 4.30 ppm and 4.11 ppm attributed to —CH$_2$—CH(OH)—CH$_2$—. The signal splitting might be explained, possibly, by the hindered rotation of the main chain in polymer molecules producing two relatively stable conformers in which methyne groups experience different environments, thereby giving rise to two peaks in NMR spectra [Reference 38] Following assignments were made to 13C-NMR spectra: chemical shift at 32.06 ppm belongs to the carbon associated with disulfide group (—CH$_2$—CH$_2$—S—S—CH$_2$—CH$_2$— and H$_2$N—CH$_2$—CH$_2$—S—S—), the shift 33.5 ppm belongs to the carbon associated with disulfide group near the tertiary amine >N—CH$_2$—CH$_2$—S—S—. The shifts at 38.83 ppm and 42.33 ppm belong to the carbon associated with primary amino group (NH$_2$—CH$_2$—CH$_2$—S—S—) and (NH$_2$—CH$_2$—CH(OH)—CH$_2$—), respectively, while the shifts at 50.58 ppm and 46.25 ppm are related to the carbon attached to secondary amines (—NH—CH$_2$—CH(OH)—CH$_2$—) and (—CH$_2$—S—S—CH$_2$—CH$_2$—NH—CH$_2$—), respectively. The shift at 53.2 ppm and 58.84 ppm is related to the carbon next to tertiary amino group (N(CH$_2$—CH(OH)—CH$_2$-)$_3$) and >N—CH$_2$—CH$_2$—S—S—, and that at 64.85-63.56 ppm belongs to the carbon associated with hydroxyl group (—CH$_2$—CH(OH)—CH$_2$—). Since tertiary amino group represents the branching point on PHPI-SS [Reference 36], the degree of branching was calculated by the ratio of secondary to tertiary amino groups (Table 1). It was determined that approximately every second repeating unit of PHPI—SS has a branching point, i.e. these polymers are highly branched.

The presence of cystamine moieties and disulfide linkages in the polymers was proven by NMR spectroscopy, elemental analysis and chemical determination of disulfide groups. Experimental molar ratio between 2-hydroxypropylene imine and ethylenedithioethylene imine segments in PHPI-SS (HPI/EDEI) determined by different methods (Table 2) is in good agreement with the theoretical ratio HPI/EDEI calculated according to the initial feed of the monomers (Table 1). The most reliable results gave $^1$H-NMR spectroscopy. The ratio HPI/EDEI calculated from the experimentally determined content of the disulfide groups close to theoretical value means that PHPI-SS do have disulfide linkages but not thiol groups, i.e. the polymers did not degrade during the synthesis and purification.

TABLE 2

Ratio of HPI/EDEI in various PHPI-SS

| | | Experimental HPI/EDEI calculated from: | | | |
|---|---|---|---|---|---|
| Polymer | HPI/EDEI[a] | $^1$H-NMR | $^{13}$C-NMR | EA[b] | ChADG[c] |
| PHPI-SS1 | 1 | 0.98 | 1.19 | 0.59 | 0.87 |
| PHPI-SS2 | 1.85 | 1.93 | 2.29 | 1.76 | 2.16 |
| PHPI-SS3 | 3 | 2.98 | 3.20 | 2.98 | 2.63 |

Figure 4:
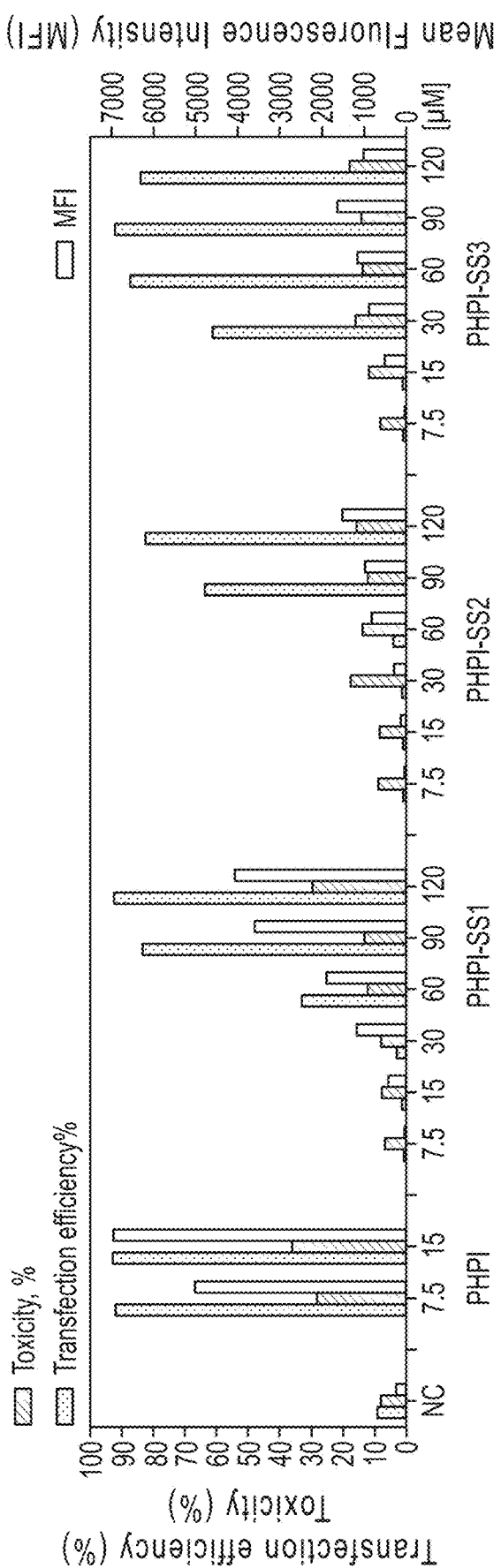
FIG. 4 provides analysis of biodegradable polymer ability to deliver DNA into the cell. Each polymer concentration ranges [μM] are indicated in the X-axis. Transfection efficiency (GFP$^+$ cell %) and toxicity are plotted on the left Y-axis, MFI—on the right Y-axis.

[a] ratio in the initial feed;
[b] elemental analysis: content of sulfur;
[b] content of disulfide groups Example 2. Gene Delivery Mediated by Biodegradable Polymers Transfection experiments were performed to characterize the newly synthesized biodegrable polymers and to determine an optimal polymer concentration for further experiments. GFP expression analysis (FIG. 4) showed that efficiency of PHPI-SS1, PHPI-SS2 and PHPI-SS3 was comparable to that of PHPI, the use of these polymers gave similar results with GFP$^+$ cell percent reaching 80-90%. Transgene expression level (presented as mean fluorescence intensity, MFI) for none of biodegradable polymers reached the level (6900 units) established by PHPI-mediated transfection. However, cytotoxicity levels for the tested polymers (PHPI-SS1, PHPI-SS2 and PHPI-SS3) were lower than that of PHPI suggesting that polymer ability to degrade within the cell contributes to the better health and survival of the cells.

Example 3. Analysis of DNA-Polymer Complexes by DLS

Figure 5:
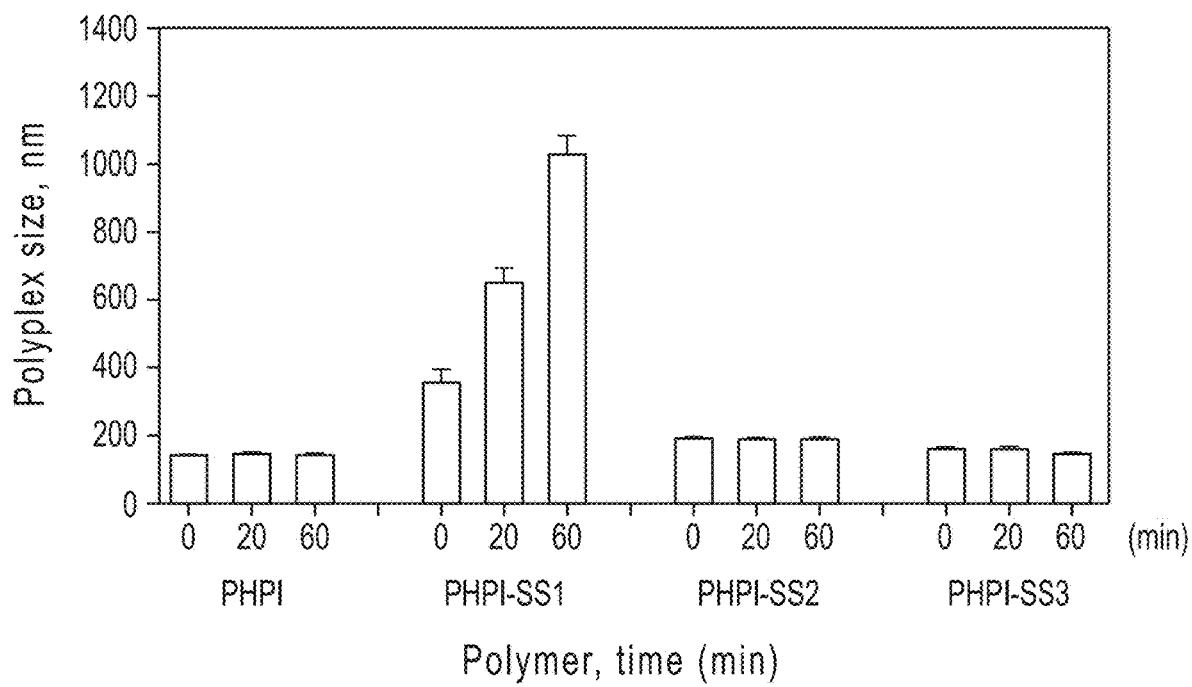
FIG. 5 provides analysis of PHPI-SS-DNA polyplexes by DLS. The time of incubation is shown on X axis, Data shows particle size mean values±SD (n=3).

Using the information acquired from transfection studies, i.e. knowing specific polymer concentration that ensures strong transgene expression we next analyzed DNA-polymer complexes by DLS (FIG. 5). From literature reviews

[Reference 39] is known that larger complexes are internalized via different pathway than smaller ones (macropinocytosis vs. endocytosis), and for this reason processed differently leading to differences in transgene expression. DLS analysis revealed that PHPI-SS2 and PHPI-SS3 formed complexes of similar size as PHPI (~150 nm), whereas PHPI-SS1 generated complexes were significantly larger (400-600 nm) and unstable, with polyplex size increasing with time.

Example 4. DNA Binding and Release Study

Figure 6:
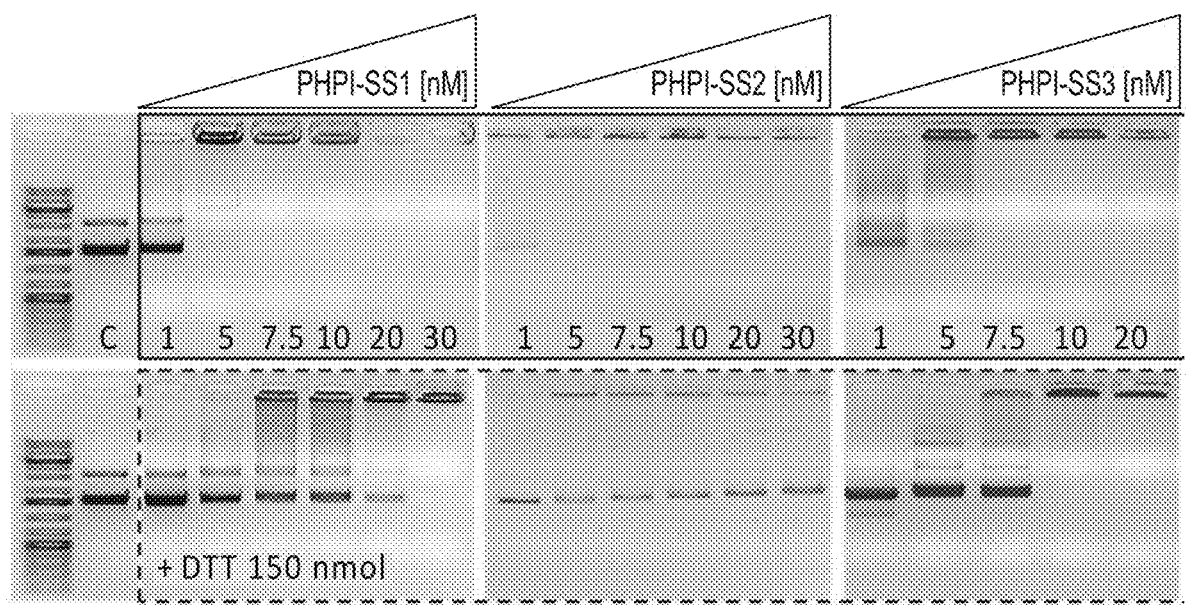
FIG. 6 provides DNA binding and release analysis. DNA-polymer complexes were resolved on 1% agarose gel (no DTT added upper—panel, +DTT, lower panel). C—control sample, (1 μg plasmid DNA); 1-30 indicates polymer concentration (nM) in each sample.

To better understand the differences observed in transfection results we further analyzed biodegradable polymer ability to break down and release DNA following reducing agent DTT treatment. The upper panel (FIG. 6) shows polymer ability to bind DNA (polymer concentration range 1-30 nM); DNA-polymer complexes did not migrate out of the agarose gel well. PHPI-SS2 fully complexed DNA even at the lowest concentrations, while PHPI-SS1 and PHPI-SS3 reached this capacity only at 5 and 7.5 nM concentrations, respectively. However, following DTT treatment (lower panel) only these two polymers fully released DNA and we observed it migrating in the agarose gel. At higher polymer concentrations (10-30 nM), nonetheless, DTT was not able to release DNA from the complex. PHPI-SS2 was clearly affected by DTT treatment, yet released only part of DNA, the rest stayed in the gel. These data corroborates transfection results showing that the most promising polymers are PHPI-SS1 and PHPI-SS3. These two polymers were further analyzed by gel filtration to better understand their degradation process.

Example 5. Polymer Degradation Studies

Figure 7A:
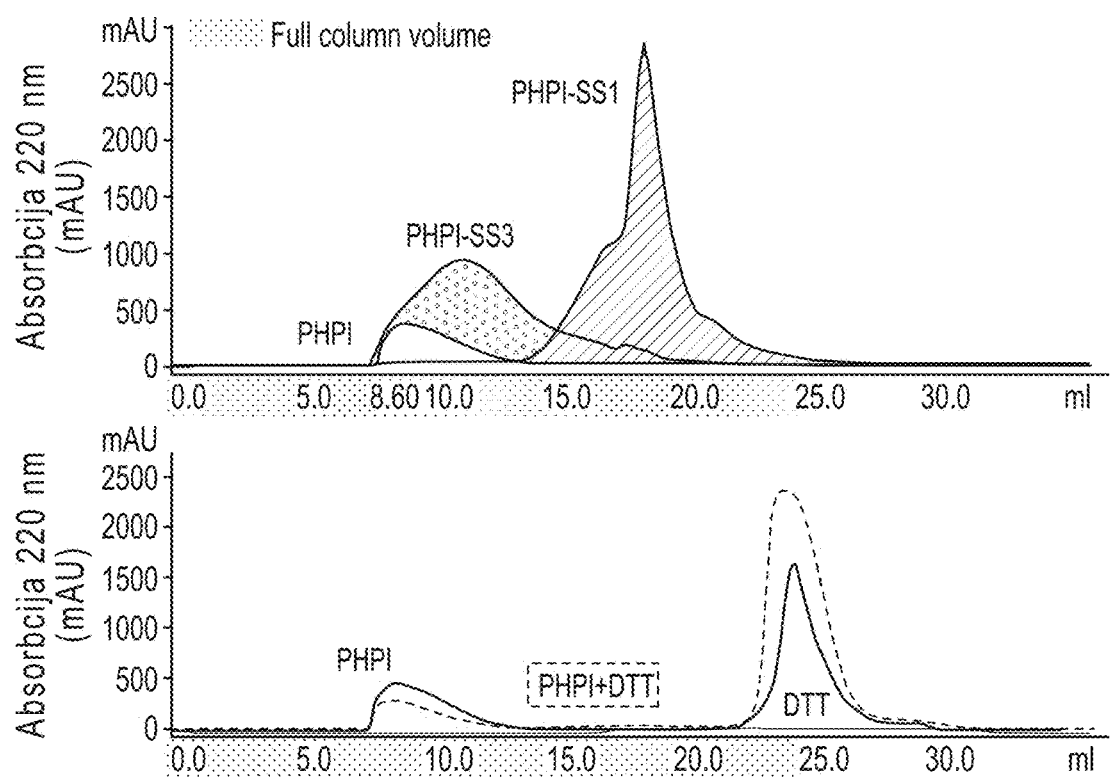
FIGS. 7A and 7B show PHPI-SS1 and PHPI-SS3 polymer degradation analysis by gel chromatography.
Figure 7B:
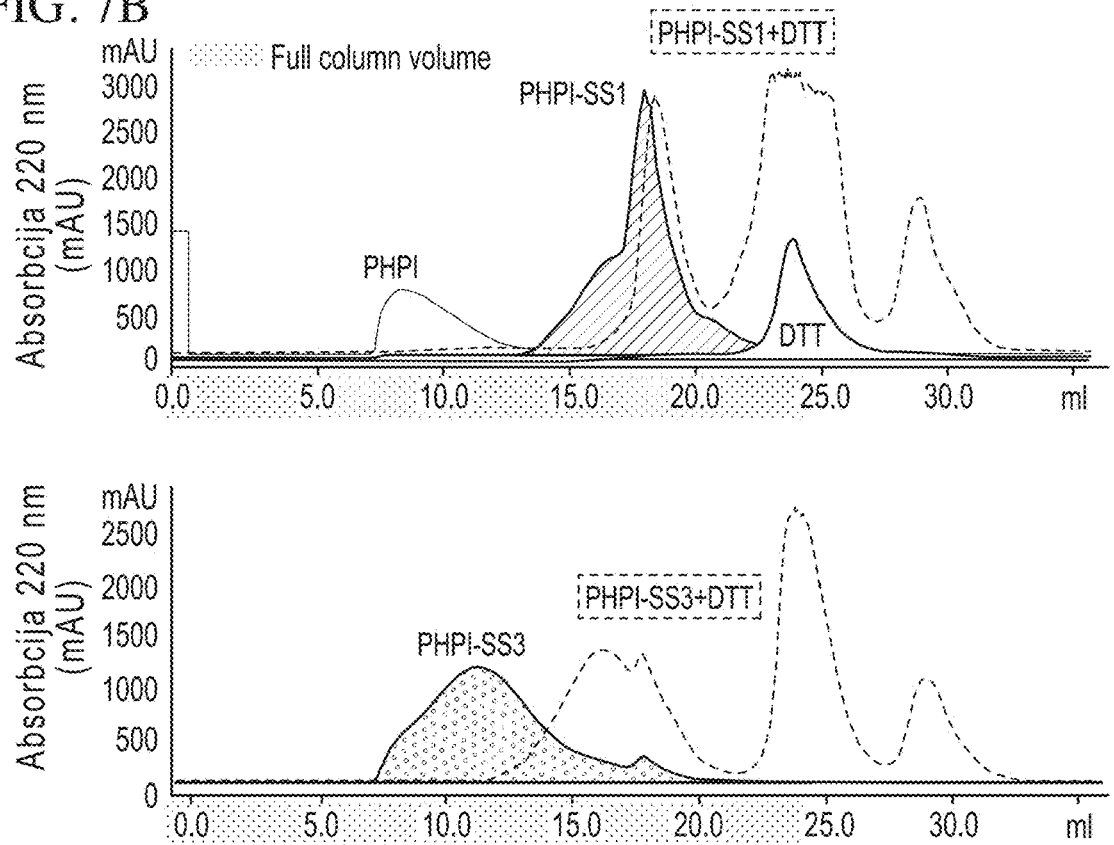

Degradation of PHPI-SS1 and PHPI-SS3 was analysed using liquid chromatography system. Prior to DTT treatment gel filtration profiles were determined for each polymer and DTT separately. Based on the data in FIG. 7A, PHPI-SS3 is similar to PHPI by length while PHPI-SS1 is composed of significantly shorter chains. DTT came out further than the full volume of the column and can be clearly distinguished from the polymers. PHPI did not degrade upon DTT treatment (FIG. 7B) while PHPI-SS3 and the polymer with shorter chains PHPI-SS1 were broken down to oligomers and monomers.

Example 6. RNA Purification after Transfection

Figure 8A:
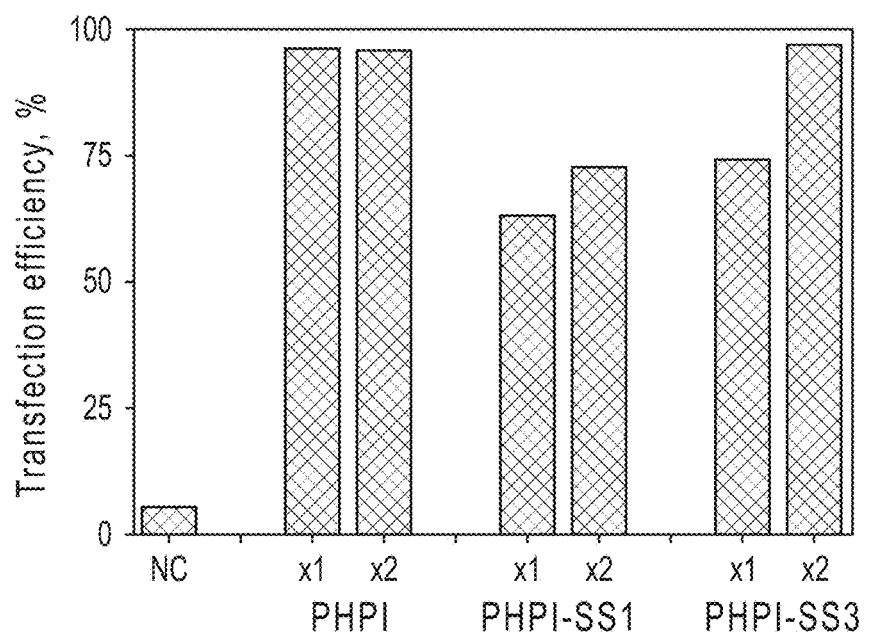
FIGS. 8A and 8B show RNA recovery after transfection by PHPI and its biodegradable derivatives.
Figure 8B:
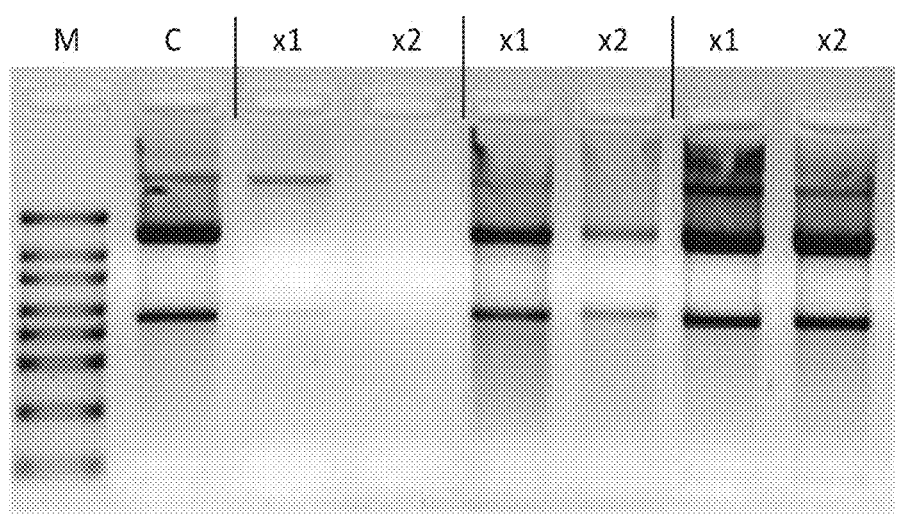

RNA purification is oftenly performed after the transfection in order to determine gene expression levels by qPCR, RT-PCR. Here RNA levels are studied following its extraction after the transfection. HEK-293 cells were transfected twice within 24 h period with EGFP reporter plasmid. Cells were analyzed 24 h after each transfection: half of the cells were used for flow cytometry to evaluate transfection efficiency, the other half were used for RNA purification. As seen in FIG. 8A, transfection efficiency for all the samples reached 60-95%, and increased slightly after the second transfection. RNA recovery (FIG. 8B) from PHPI-transfected cells was poor after the first transfection and worse after the second.

RNA recovery from biodegradable polymer transfected cells was better (especially with PHPI-SS3). PHPI has the ability to efficiently deliver transgene into the cells and facilitate efficient gene expression; however, appeared to have a significant drawback of binding RNA in the cytosol and by that hampering subsequent analysis. Biodegradable polymers disintegrate within the cells under the influence of reducing environment; RNA recovery is not significantly affected. PHPI-SS1 showed promising results, however, seemed to bind RNA once more polymer was getting inside (after the second transfection). RNA recovery from PHPI-SS3 transfected cells was not affected even after the double transfection suggesting that this polymer could be a great candidate for commercialization.

V. Conclusions

Poly(2-hydroxypropylene imines) containing segments of cystamine PHPI-SS were synthesized by polycondensation of 1,3-diamino-2-propanol and 1,3-dibromo-2-propanol in the presence of cystamine in different molar ratio. Molecular weight of PHPI-SS was relatively low, $M_w$ 3.9 to 7.9 kDa, and these polymers were highly branched, irrespective of the cystamine content. Data of chemical analysis and NMR spectra revealed that composition of PHPI-SS was close to expectations, and these polymers had disulfide linkages. DLS analysis revealed that PHPI containing segments of cystamine, PHPI-SS, formed complexes of similar size as PHPI (~150 nm). GFP expression analysis showed that efficiency of the novel transfection reagents was comparable to that of PHPI and reached 80-90%. Cytotoxicity levels for PHPI-SS were lower than that of PHPI. PHPI containing segments of cystamine disintegrated within the cells under the treatment of the reducing agent DTT, i.e. they were biodegradable. RNA recovery from PHPI-SS transfected cells was not affected even after the double transfection suggesting that this polymer could be a great candidate for in vitro and in vivo transfection.

VI. References

1. L. Huang, E. Viroonchatapan, Introduction, in: L. Huang, M. Wagner (Eds.), Academic Press, New York, 1999, 3-22.
2. I. M. Verma, N. Somia, Nature 389 (1997) 239-242.
3. D. T. Curiel, S. Agrawal, E. Wagner, M. Cotton, Proc. Natl. Acad. Sci. USA 88 (1991) 8850-8854.
4. C. M. Liu, D. P. Liu, W. J. Dong, C. C. Liang, Biochem. Biophys. Res. Commun. 313 (2004) 716-720
5. P. L. Felgner, T. R. Gadek, M. Holm, R. Roman, H. W. Chan, M. Wenz, J. P. Northrop, G. M. Ringold, M. Danielsen, Proc. Natl. Acad. Sci. USA 84 (1987) 7413-7417.
6. S. C. De Smedt, J. Demeester, W. E. Hennink, Pharm. Res. 17 (2000) 113-126.
7. M. J. Tiera, F. O. Winnik, J. C. Fernandes, Curr. Gene Ther. 6 (2006) 59-71.
8. M. D. Brown, A. G. Schatzlein, I. F. Uchegbu, Int. J. Pharm. 229 (2001) 1-21.
9. X. Gao, K. S. Kim, D. Liu, AAPS J. 9 (2007) E92-E104.
10. C. Louise, Methods Mol. Biol. 333 (2006) 201-226.
11. J. K. Vasir, V. Labhasetwar Expert Opin. Drug Deliv. 3 (2006) 325-344.
12. P. Dubruel, E. Schacht, Macromol. Biosci. 6 (2006) 789-810.
13. T. Merdan, J. Kopecek, T. Kissel, Adv. Drug Del. Rev. 54 (2002) 715-758.
14. O. Boussif, F. Lezoualc'ht, M. A. Zanta, M. D. Mergnyt, D. Schermant, B. Demeneixt, J. P. Behr, Proc. Natl. Acad. Sci. Usa 92 (1995) 7297-7301.
15. M. Thomas, A. M. Klibanov, Appl Microbiol Biotechnol 62 (2003) 27-34

16. X. Zhang, W. T. Godbey, Adv. Drug Deliv. Rev. 58 (2006) 515-534.
17. D. Ibraheem, A. Elaissari, H. Fessi, Int. J. Pharm. 459 (2014) 70-83
18. D. C. Gorecki, Expert Opin. Emerging Drugs 6 (2001) 187-198.
19. D. G. Anderson, D. M. Lynn, R. Langer. Angew. Chem. Int. Ed. 42 (2003) 3153-3158.
20. D. M. Lynn, M. M. Amiji, R. Langer. Angew. Chem. Int. Ed. 402001; 1707-1710.
21. D. M. Lynn, D. G. Anderson, D. Putnam, R. J. Langer, Am Chem Soc 123 (2001) 8155-8156.
22. Y. B. Lim, S. M. Kim, H. Suh, J. S. Park, Bioconjugate Chem. 13 (2002) 952-957.
23. M. Wei, D. Good, Novel Gene Therapy Approaches, in: Y. Kim, C. Zhang, C. Cho, M. Cho, H. Jiang, InTech, 2013, p. 375-396.
24. N. Lavignac, M. Lazenby, P. Foka, B. Malgesini, I. Verpilio, P. Ferruti, R. Duncan. Macromol Biosci 4 (2004) 922-929.
25. S. C. Richardson, N. G. Pattrick, Y. K. Man, P. Ferruti, R. Duncan. Biomacromolecules, 2 (2001) 1023-1028.
26. V. Bulmus, M. Woodward, L. Lin, N. Murthy, P. Stayton, A. Hoffman, J Controlled Release 93 (2003) 105-120.
27. F. Meng, W. E. Hennink, Z. Zhong, Biomaterials 30 (2009) 2180-2198
28. L. V. Christensen, C. W. Chang, W. J. Kim, S. W. Kim, Z. Zhong, C. Lin, et al. Bioconjug Chem 171 (2006) 1233-1240.
29. C. Lin, Z. Zhong, M. C. Lok, X. Jiang, W. E. Hennink, J. Feijen, J. F. Engbersen, Bioconjugate Chem 18 (2007) 138-145.
30. F. Martello, M. P. Johan, F. J. Engbersen, P. Ferruti, Journal of Controlled Release 164 (2012) 372-379.
31. Q. Peng, Z. Zhong, R. Zhuo, *Bioconj. Chem.* 19 (2008) 499-506.
32. M. A. Gosselin, W. Guo, R. J. Lee, *Bioconj. Chem.* 12 (2001) 989-994.
33. M. Breunig, U. Lungwitz, R. Liebl, A. Goepferich, *Proc. Natl. Acad. Sci. USA* 104 (2007) 14454-14459.
32. S. Son, R. Namgung, J. Kim, K. Singha, W. J. Kim, Accounts Of Chemical Research, 45 (2012) 1100-1112
34. Y. X. Sun, X. Zeng, Q. F. Meng, X. Z. Zhang, S. X. Cheng, R. X. Zhuo, *Biomaterials* 29 (2008) 4356-4365.
35. L. Zaliauskiene, U. Bernadisiute, A. Vareikis, R. Makuska, I. Volungeviciene, A. Petuskaite, L. Riauba, A. Lagunavicius, S. Zigmantas, Bioconjugate Chem 21 (2010) 1602-1611.
36. A. Bockuviene, A. Vareikis, R. Makuska, Chemija 26 (2015) 51-59.
37. C. R. Stahl, S. Siggia, Anal. Chem., 29 (1957) 154-155.
38. J. M. Cheng, J. P. Heller, K. A. Petterson, J. D. Roberts. Magn. Reson. Chem. 40 (2002) 666-671.
39. C. Scholz, E. Wagner, Journal of Controlled Release 161 (2012) 554-565.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A cationic polymer resulting from the polymerization of:
   (a) a 1,ω-dibromoalkyl monomer; and
   (b) a ω,ω'-diaminoalkyl disulfide monomer having two terminal carbon groups, wherein each terminal carbon comprises a substituent group that is —NH$_2$, and optionally;
   (c) a 1,ω-diaminoalkyl monomer.

2. The cationic polymer of claim 1, resulting from the polymerization of
   (a) said 1,ω-dibromoalkyl monomer; and
   (b) said ω,ω'-diaminoalkyl disulfide monomer, and
   (c) said 1,ω-diaminoalkyl monomer.

3. The cationic polymer of claim 2, wherein
   said 1,ω-dibromoalkyl monomer is $$\text{Br-L}^{M1}\text{-Br} \quad (M1);$$

said ω,ω'-diaminoalkyl disulfide monomer is $$\text{H}_2\text{N-L}^{M2A}\text{-S—S-L}^{M2B}\text{-NH}_2 \quad (M2); \text{ and}$$

said 1,ω-diaminoalkyl monomer, when present, is $$\text{H}_2\text{N-L}^{M1}\text{-NH}_2 \quad (M3);$$

wherein
   each $L^{M1}$, $L^{M2A}$ and $L^{M2B}$ is independently substituted or unsubstituted alkylene.

4. The cationic polymer of claim 1, wherein the monomers are present in a ratio of the 1,ω-dibromoalkyl monomer: ω,ω'-diaminoalkyl disulfide monomer: 1,ω-diaminoalkyl monomer, and wherein the ratio is about: 1:1:0; 1:0.9:0.1; 1:0.8:0.2; 1:0.75:0.25; 1:0.7:0.3; 1:0.6:0.4; 1:0.5:0.5; 1:0.4:0.6; 1:0.3:0.7; 1:0.25:0.75; 1:0.2:0.8; or 1:0.1:0.9.

5. The cationic polymer of claim 1, wherein said ω,ω'-diaminoalkyl disulfide monomer is cystamine (CT).

6. The cationic polymer of claim 1, wherein said 1,ω-dibromoalkyl monomer is substituted with a hydroxyl group.

7. The cationic polymer of claim 6, wherein said 1,ω-dibromoalkyl monomer is 1,3-dibromo-2-propanol (DBP).

8. The cationic polymer of claim 1, wherein said 1,ω-diaminoalkyl monomer is substituted with a hydroxyl group.

9. The cationic polymer of claim 8, wherein said 1,ω-diaminoalkyl monomer is 1,3-diamino-2-propanol (DAP).

10. The cationic polymer of claim 1, resulting from the polymerization of
    (a) 1,3-dibromo-2-propanol (DBP); and
    (b) cystamine (CT);
    wherein the ratio of DBP:CT is about: 1:1; 0.9:0.1; 0.8:0.2; 0.7:0.3; 0.6:0.4; 0.4:0.6; 0.7:0.3; 0.8:0.2; or 0.9:0.1.

11. The cationic polymer of claim 10, wherein the ratio of DBP:CT is about 1:1.

12. The cationic polymer of claim 1, resulting from the polymerization of
    (a) 1,3-dibromo-2-propanol (DBP);
    (b) cystamine (CT); and
    (c) 1,3-diamino-2-propanol (DAP);
    wherein the ratio of DBP:CT:DAP is about: 1:0.9:0.1; 1:0.8:0.2; 1:0.75:0.25; 1:0.7:0.3; 1:0.6:0.4; 1:0.5:0.5; 1:0.4:0.6; 1:0.3:0.7; 1:0.25:0.75; 1:0.2:0.8; or 1:0.1:0.9.

13. The cationic polymer of claim 12, wherein the ratio of DBP:CT:DAP is about 1:0.7:0.3 or 1:0.5:0.5.

14. The cationic polymer of claim 1, wherein said cationic polymer is linear.

15. The cationic polymer of claim 1, wherein said cationic polymer is branched.

16. The cationic polymer of claim 1, having a weight average molecular weight (Mw) of about 4,000; 5,000; 6,000; 7,000; 8,000; 9,000; 10,000; 12,000; 14,000; 16,000; 18,000; or 20,000.

\* \* \* \* \*